United States Patent [19]

Romero-Sierra et al.

[11] 4,349,580

[45] Sep. 14, 1982

[54] PROCESS AND SOLUTION FOR PRESERVING GREEN PLANT TISSUES

[75] Inventors: César Romero-Sierra, Bath; John C. Webb, Kingston, both of Canada

[73] Assignee: Queen's University at Kingston, Kingston, Canada

[21] Appl. No.: 265,710

[22] Filed: May 21, 1981

Related U.S. Application Data

[63] Continuation-in-part of Ser. No. 61,688, Jul. 30, 1979, Pat. No. 4,278,715.

[51] Int. Cl.$^3$ .......................... A01N 3/00; C09K 15/06
[52] U.S. Cl. .................................... 427/4; 47/DIG. 2; 252/400 R
[58] Field of Search ....................... 427/4; 252/400 R; 47/DIG. 2; 71/68

[56] References Cited

U.S. PATENT DOCUMENTS 2,567,929 9/1951 Fessender ............................ 427/4

Primary Examiner—Sam Silverberg
Attorney, Agent, or Firm—Richard J. Hicks; Stanley E. Johnson

[57] ABSTRACT

A process for preserving green colored plant tissues while retaining the natural green color thereof, in which the tissues are immersed in a relatively inexpensive solution comprising up to about 90% water, at least one monohydric alcohol, at least one preservative component such as sulphurous acid, and sufficient buffering and mordant reagents such as citric acid and cupric salts such as cupric chloride and cupric sulphate, to control the pH and osmolality of the solution and so as to permanently retain the natural green color in the tissues.

4 Claims, No Drawings

PROCESS AND SOLUTION FOR PRESERVING GREEN PLANT TISSUES

CROSS REFERENCE TO RELATED APPLICATIONS

This application is a continuation-in-part of our earlier filed U.S. application Ser. No. 061,688 filed July 30, 1979 now U.S. Pat. No. 4,278,715 entitled "Preservation of Green Plant Tissues".

Field of Invention

This invention relates to the preservation of green plant tissues and more particularly to a novel composition of matter for the preservation of the natural green colour in leaves, stems and the like of flowers, shrubs, trees and the like and the preserved product.

Background of Invention

In our prior application referred to above, the disclosure of which is incorporated herein by reference, there is described a process and composition of matter for preserving green coloured plant tissue while retaining the natural green colour thereof, in which the tissues are immersed in a solution comprising 30–70% by volume water; at least one monohydric alcohol; at least one preservative component selected from the group comprising lower carboxylic acids, and di and trihydric alcohols, and sufficient buffering and mordant reagents to control the pH and osmolality of the solution so as to permanently retain the green colour in the tissues. While this solution produces generally satisfactory results for almost all kinds of green leaves, it is somewhat expensive to produce as it is relatively concentrated. We have now found that relatively more dilute solutions than heretofore employed may be employed with equally good results, provided the compositions contain relatively larger quantities of cupric salts than heretofore employed.

Brief Description of Invention

Thus, by one aspect of this invention there is provided a process for preserving naturally green coloured plant tissues comprising immersing said tissues in a solution comprising about 70–90% by volume water
5–20% by volume of a monohydric alcohol
5–15% by water sulphurous acid and containing 15–25 gms cupric chloride
20–30 gms cupric sulphate and
5–12 gms citric acid per liter of solution, for a sufficient time to effect exchange of water naturally contained in said tissues with said solution, thereby biologically preserving and fixing the green colour in said tissue.

Detailed Description of Invention

The preservation of green plant tissue specimens is considerably more difficult than preservation of relatively fibrous flowers and the like. Firstly, the cellulose and similar materials in green plant tissues form a relatively rigid framework into which the cells are arranged. The cells are, however, fully turgid only when filled with water and once this water is lost they collapse and the weight of tissues is too great for the relatively small amount of fibre to support. When this happens wilting occurs when the tissue dries out completely, rigidity is restored due to the loss of weight and the loss of lubrication between fibres. In succulents there is so little fibre that complete dehydration and rigidity is almost impossible to achieve. The dehydration process must be complete before the tissue is removed from its physical supporting medium. Failure to ensure this results in loss of shape and chemical reactions which ultimately result in tissue discoloration. Secondly, the green coloration is due to the presence of chlorophyll which is a highly reactive and sensitive substance, and unless considerable care is taken with the dehydration process, degradation of the chlorophyll occurs. It is therefore necessary to effect dehydration in such a way as to retain the original colour and shape substantially intact and subsequently treat the dehydrated tissue with a preservative to make it last.

As discussed in our related application, we have found that rather than dehydrate leaves or other green plant tissue and then preserve the dried tissues, it is preferable to effect an exchange process wherein the naturally contained water in the tissue is exchanged with a water based treatment solution containing sufficient chemical reagents to biologically preserve and environmentally fix the green colours. Buffers and the like may be added to modify the effects of the primary chemicals.

Thus, it has been found that a suitable treatment solution for green plant tissues must contain four essential groups of chemicals which may be defined as:

(a) water;
(b) an exchange medium,
(c) preservatives; and
(d) buffers, mordants and modifiers.

Throughout this specification, when referring to "water" it is implicit that distilled water is normally employed, in order to ensure uniformity or results and to provide a readily controlled standard, but it will be appreciated that distillation is not an essential characteristic of the water employed, other forms such as deionized water being equally effective. The "exchange medium" used in the present inventions is normally one or more monohydric alcohols containing 1–6 carbon atoms. Such alcohols, particularly ethyl alcohol, isopropyl alcohol and tertiary butyl alcohol are known to have considerable dehydration properties and, without wishing to be bound by this explanation, it is believed that in the present invention the alcohol or mixtures of alcohols selected causes dehydration of the natural water contained in the plant tissue and the simultaneous replacement thereof by the chemical-containing water of the inventive solutions of the alcohols listed, tertiary butyl alcohol is extremely harsh and may damage leafy tissue and for this reason is normally used in admixture with a milder alcohol such as 1-propanol. Ethyl alcohol, on the other hand may be used alone.

The preservative elements include biological preservatives and fixers and environmental fixers, such as sulphurous acid.

The buffers, mordants and modifiers include citric acid and cupric salts such as cupric chloride and cupric sulphate. The amounts of each chemical required depends upon the type of leaf being treated, the exchange medium being used and other factors. Some chemicals appear to act as colour mordants while others are buffers not only for pH but also for osmolality. The pH range is not considered critical and although the bath is generally maintained in the range 6–8, i.e. substantially neutral, pH as low as about 2 may also be employed.

Preferred treatment solutions comprise (in amounts per liter of solution):
700–900 ml water
20–30 g cupric sulphate
15–25 g cupric chloride
5–12 g citric acid
50–200 ml ethyl alcohol
50–150 ml sulphurous acid,
and more particularly
800 ml water
25 g cupric sulphate
20 g cupric chloride
10 g citric acid
100 ml ethyl alcohol
100 ml sulphurous acid.

The procedures to be adopted for treatment of the plant tissue are simple and straightforward. Firstly a treating solution is prepared by mixing the required chemicals, preferably in the order as noted below, and then immersing the specimens in the treating solution, at ambient temperature, for 10 days to 2 weeks or even longer depending upon the specimen. For example most deciduous leaves require a relatively shorter period of time than evergreens and thick tough leaves such as holly may require as long as 30 days or even more. Very thick leaves, for example rubber leaves, may require even longer. Leaves of succulents and other species which tend to be very watery and with little fibrous structure (for example water cress) by reason of their species or method of culture are somewhat difficult to treat according to the present invention even if great care is taken with the selection of the exchange medium as it appears difficult to balance the rate of exchange of natural water with the treating solution. Generally, upon immersion in the bath the colour of the leaves changes, usually to a lighter green, then as the treatment solution replaces the natural water the colour reverts to an "ideal" colour and on continued immersion the colour darkens. Following treatment in the treating solution, the specimens may be air dried and stored for use as required. Such treated specimens are best used (for teaching or similar purposes) within 2 to 3 weeks as they tend to dry out after that time. If it is desired to preserve the specimens for later use (i.e. spring or summer leaves for use as teaching aids in mid winter) or for permanent display, a secondary treatment in a "holding solution" is required. The holding solution is a glycerin/water solution preferably containing 100–700 ml glycerin per liter of water. The specimens are merely immersed and soaked in the holding solution for 2–3 weeks, at ambient temperature and then air dried. Specimens so treated maintain their colour and flexibility for periods in excess of 1 year. In certain circumstances it may be desirable to store the specimens permanently in the holding solution, depending on the end use. There is, therefore, no practical limit to the treatment time in the holding solution.

EXAMPLE 1

A series of green leaf samples, as set forth in Table 1 below were immersed in a solution comprising 800 ml water, 100 ml ethyl alcohol, 100 ml sulphurous acid, 25 g cupric sulphate, 20 g cupric chloride, and 10 g citric acid for periods varying from 10 days to 2 weeks at ambient temperatures. After treatment the leaves were placed in a holding bath containing 650 ml white glycerin per 1000 ml distilled water for 2–3 weeks, then removed, air dried and evaluated for colour and flexibility.

TABLE I

| Specimens | Results |
| --- | --- |
| white spruce | good |
| balsam | good |
| geranium | fair |
| holly | good |
| sugar maple | good |
| silver maple | good |
| birch | good |
| white cedar | good |
| greenhouse ferns | good |
| junipers | good |
| red oak | good |
| basswood | good |
| cat-tails | good |
| beech | good |
| flowering crab | good |
| elm | good |

We claim:
1. A process for preserving naturally green coloured plant tissues comprising immersing said tissues in a solution comprising about
   70–90% by volume water
   5–20% by volume of a monohydric alcohol
   5–15% by volume sulphurous acid
and containing
   15–25 gms cupric chloride
   20–30 gms cupric sulphate and
   5–12 gms citric acid per liter of solution,
for a sufficient time to effect exchange of water naturally contained in said tissues with said solution, thereby biologically preserving and fixing the green colour in said tissue.

2. A process as claimed in claim 1 wherein said solution comprises about 80% by volume water 10% by volume ethyl alcohol, 10% by volume sulphurous acid and contains 25 gms cupric sulphate, 20 gms cupric chloride and 10 gms citric acid per liter.

3. A solution, for the preservation of naturally green coloured plant tissues, consisting essentially of
   70–90% by volume water
   5–20% by volume of a monohydric alcohol
   5–15% by volume sulphurous acid
and which contains
   15–25 gms cupric chloride
   20–30 gms cupric sulphate and
   5–12 gms citric acid, per liter of solution.

4. A solution as claimed in claim 3 consisting essentially of 80% by volume water, 10% by volume ethyl alcohol, 10% by volume sulphurous acid and containing 25 gms cupric sulphate, 20 gms cupric chloride and 10 gms citric acid per liter.

* * * * *